United States Patent
Kasasbeh

(10) Patent No.: US 8,403,869 B2
(45) Date of Patent: Mar. 26, 2013

(54) SIDE-DEPLOYED MEDICAL GUIDEWIRE TORQUER

(75) Inventor: Ehab Saleh Kasasbeh, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 13/339,551

(22) Filed: Dec. 29, 2011

(65) Prior Publication Data
US 2012/0172845 A1 Jul. 5, 2012

Related U.S. Application Data

(60) Provisional application No. 61/428,773, filed on Dec. 30, 2010.

(51) Int. Cl.
*A61B 5/00* (2006.01)
(52) U.S. Cl. ...................................................... 600/585
(58) Field of Classification Search ................... 600/585
See application file for complete search history.

(56) References Cited

U.S. PATENT DOCUMENTS

| 2005/0070820 A1* | 3/2005 | Boutillette et al. ........... 600/585 |
| 2005/0096566 A1* | 5/2005 | Arnott ........................... 600/585 |
| 2009/0254001 A1* | 10/2009 | Wright et al. .................. 600/585 |

* cited by examiner

*Primary Examiner* — Max Hindenburg
(74) *Attorney, Agent, or Firm* — Tarolli, Sundheim, Covell & Tummino LLP

(57) ABSTRACT

A side-deployable medical guidewire or guide wire torquer, torque device or wire manipulator. The torquer comprises an elongate body comprising first and second halves having an outer surface and inner surfaces, wherein the first and second halves are coupled to one another such that the inner surfaces to mate with one another, and wherein the mated surfaces are substantially parallel to the longitudinally axis of the body; a plurality of wire retainers disposed on the inner surfaces of one or more of the first and second halves configured to engage a guidewire positioned between the halves; and a releasable lock mechanism configured to mechanical secure the first and second halves in the mated configuration.

17 Claims, 4 Drawing Sheets

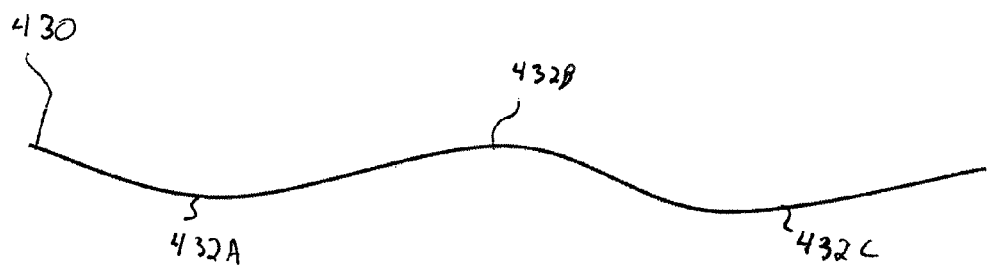
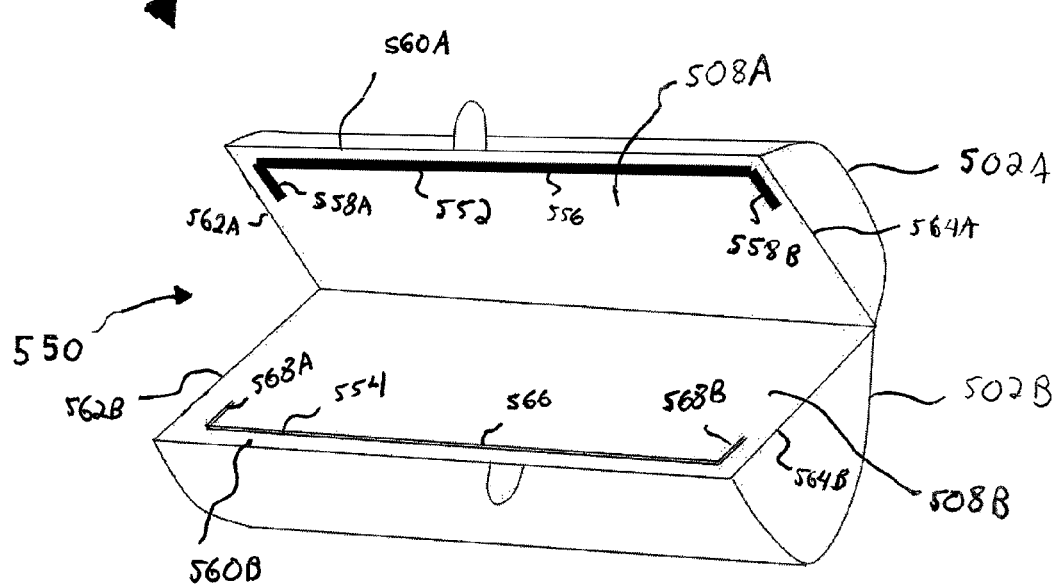

SIDE-DEPLOYED MEDICAL GUIDEWIRE TORQUER

CROSS-REFERENCE TO RELATED APPLICATIONS

This application claims priority from U.S. Provisional Patent Application No. 61/428,773, filed on Dec. 30, 2010. The contents of this application are hereby incorporated by reference herein.

BACKGROUND

1. Field of the Invention

The present invention is generally directed to the control of a medical guidewire, and more particularly, to a side-deployed medical guidewire torquer.

2. Related Art

As is well known, a guide wire or guidewire is a flexible metallic wire inserted into a patient that is commonly used in a number of a different medical procedures. For example, guidewires are used in vascular surgery, neurosurgery, to position catheters, endotracheal tubes, or gastric feeding tubes, to localize tumors, etc. One particular use for guidewires is in the catheter based treatment of heart disease, known as interventional cardiology. In one specific interventional cardiology procedure, a guidewire is introduced into any large peripheral artery or vein, and is advanced to a site of stenosis. After the guidewire is positioned, a catheter is introduced along the path of the guidewire. In other procedures, the guidewire may be used independent from a catheter or may be positioned in the patient following positioning of a catheter.

Guidewires are relatively fine and difficult to grip between a surgeon's fingers, thereby making the positioning of the guidewire challenging. As such, a device called a wire manipulator, torque device or simply "torquer" is often affixed to the wire and allows the surgeon to more precisely control movement of the wire and to negotiate the various turns and branches of the cardiovascular system. That is, the torquer allows the surgeon to apply torque so as to manipulate the distal end of the guide wire. In addition to its use in the field of interventional cardiology, such torquers may also be used in vascular procedures, neurosurgical procedures, interventional radiological procedures.

Generally, conventional guidewire torquers are configured to be attached from the proximal end of the guidewire. Specifically, most conventional guidewire torquers are threaded onto the proximal end of the guidewire, and then advanced along the wire until a suitable location is reached. Such a guidewire torquer is then clamped or secure to the guidewire at the suitable location.

SUMMARY

In one aspect of the present invention, a side-deployable medical guidewire torquer is provided. The torquer comprises an elongate body comprising first and second halves having an outer surface and inner surfaces, wherein the first and second halves are coupled to one another such that the inner surfaces to mate with one another, and wherein the mated surfaces are substantially parallel to the longitudinally axis of the body; a plurality of wire retainers disposed on the inner surfaces of one or more of the first and second halves configured to engage a guidewire positioned between the halves; and a releasable lock mechanism configured to mechanical secure the first and second halves in the mated configuration In another aspect of the present invention, a method for using a guidewire torquer is provided. The method comprises: deploying the torquer from the side of a medical guidewire; manipulating the torquer to position a distal end of the guidewire in a patient; and detaching the torquer from the medical guidewire.

BRIEF DESCRIPTION OF THE DRAWINGS

Illustrative embodiments of the present invention are described herein with reference to the accompanying drawings, in which:

FIG. 4 illustrates an exemplary shape of a wire positioned in a guidewire torquer, in accordance with embodiments of the present invention;

FIG. 5 is a perspective view of an exemplary guidewire torquer, in accordance with embodiments of the present invention;

DETAILED DESCRIPTION

Aspects of the present invention are generally directed to a side-deployed medical guidewire torquer. Such a guidewire torquer is configured to engage and attach to a medical guidewire from the side of the wire, and does not need to be attached from the end of the guidewire. The side-deployable guidewire torquer in accordance with embodiments of the present invention is easier to attach to the wire than conventional torquers deployed from the proximal end of the wire, and may reduce procedure times since there is not need to advance the torquer from the end of the wire. Reducing procedure times is beneficial both to the operator (surgeon) and to the patient as it decreases complications and radiation exposure times, and may increase the procedural success rate by potentially preventing loss of position that might result from multiple exchanges of a torquer of the wire.

Figure 1:
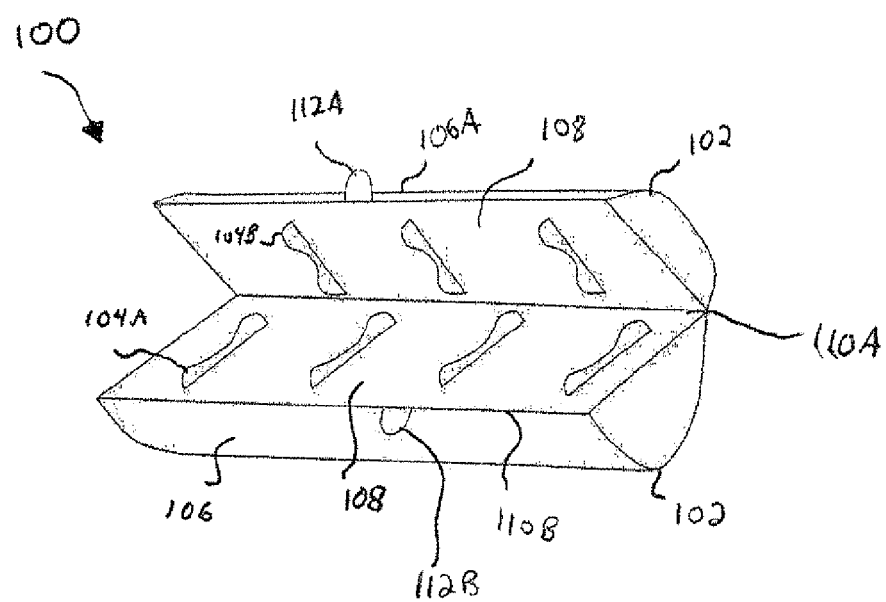
FIG. 1 is a perspective view of an exemplary guidewire torquer, in accordance with embodiments of the present invention.

FIG. 1 is a perspective view of a side-deployable medical guidewire torquer 100 in accordance with embodiments of the present invention. As shown, torquer 100 comprises an elongate body having a generally cylindrical shape. Torquer 100 is divided into first and second elongate halves 102 that are separated along a longitudinal axis of the torquer. Each half 102 comprises an outer surface 106, and an inner surface 108. Additionally, halves 102 are coupled to one another at a first edge 110A such that inner surfaces 108 mate with one another. Mating inner surfaces 108 are substantially parallel to the longitudinal axis of the device, and the body of torquer 100 opens along second elongate edge 110B.

As shown in FIG. 1, torquer 100 has a plurality of wire retainers 104 disposed on inner surfaces 108. Wire retainers 104 are configured to retain the medical guidewire in a desired location within torquer 100. In the embodiments of FIG. 1, wire retainers 104 are ribs 104 extending from the inner surfaces 108 of the first and second halves 102. During use of torquer 100, a guidewire is positioned between first and second halves 102, and halves 102 are closed together. When halves 102 are closed, ribs 104 are configured to engage the guidewire positioned between the halves. As shown in FIG. 1, ribs 104 on the first and second halves are offset from one another.

Additionally, guidewire torquer 100 includes finger handles or arms 112 that allow a surgeon to close the torquer around a wire.

As noted above, FIG. 1 illustrates embodiments of the present invention in which torquer 100 has a substantially cylindrical shape, and, as such, each half 102 of the torquer is a half of the cylinder. It would be appreciated that the shape of torquer 100 of FIG. 1 is merely illustrative and other shapes are within the scope of the present invention. For example, in alternative embodiments, torquer 100 may have a circular or elliptical shape.

Embodiments of the present invention are primarily described herein with reference to the torquer having first and second halves. It would be appreciated that the term halves is merely used to illustrate embodiments of the present invention, and is not intended to require that both of the halves be the same size. For example, in embodiments of the present invention the first half of the elongate body may be substantially larger than second half of the body and vice versa.

FIG. 1 illustrates wire torquer 100 in which first and second halves 102 are attached along the substantial entirety of edge 110A. It would be appreciated that the embodiments of FIG. 1 are merely schematic and do not limit the attachment of halves 102 to one another. For example, in embodiments of the present invention, halves 102 are connected by one or more hinges that provide a gap between the halves.

Additionally, FIG. 1 illustrates embodiments in the surfaces 102 are substantially planar. It would be appreciated that in other embodiments, one or more portions of the surface may be recessed so that halves 102 may close together properly.

Figure 2A:
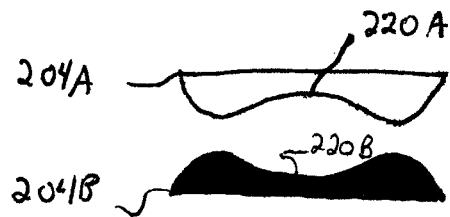
FIG. 2A is an end view of ribs of an exemplary guidewire torquer, in accordance with embodiments of the present invention.

As noted above, a plurality of wire retainers 104 may be disposed on one or both inner surfaces 108 of wire torquer 100. It would be appreciated that wire retainers 104 may have different sizes or shapes depending on the configuration of wire torquer 100. FIGS. 2A-3B illustrate two different exemplary shapes for wire retainers 104 in the form of ribs 204 extending from the surfaces 108. More specifically, FIG. 2A is an end view of two ribs 204A, 204B that may positioned on first and second halves 102 of wire torquer 100. For ease of illustration ribs 204 are shown in FIG. 2A as being substantially parallel to one another. It would be appreciated that this view of ribs 204 is merely for illustration purposes and does not limit the relationship of the two ribs to one another.

In the embodiments of FIG. 2A, ribs 204 are planar elements that extend from the inner surfaces 108 of the first and second halves 102. As shown, each rib has a concave area 220 that is proximate to the opposing half. In particular, concave areas 220 of FIG. 2A comprise concave arches 220 that engage a guidewire positioned within wire torquer 100.

Figure 2B:
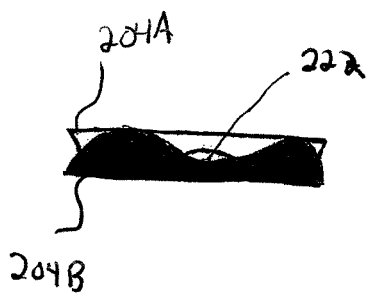
FIG. 2B is an end view of the ribs of FIG. 2A illustrating an exemplary rib overlap, in accordance with embodiments of the present invention.

As noted, FIG. 2A illustrates ribs 204 separated from one another. In contrast, FIG. 2B illustrates ribs 204 in a closed position. That is, FIG. 2B illustrates the position of ribs 204 relative to one another when halves 102 of wire torquer are mated or closed together. Ribs 204 are offset from one another such that, in the end view of FIG. 2B, rib 204B is positioned in front of rib 204A. Additionally, when ribs 204 are in the closed position, the ribs are configured to engage and securely retain a section of the guidewire within torquer 100. More specifically, when ribs 204 are in the closed position, the convex arches 220 create a space 222 in which the guidewire is positioned. In the embodiments of FIGS. 2A and 2B, the guidewire is retained entirely between ribs and does not contact the inner surfaces of the torquer halves.

Figure 3A:
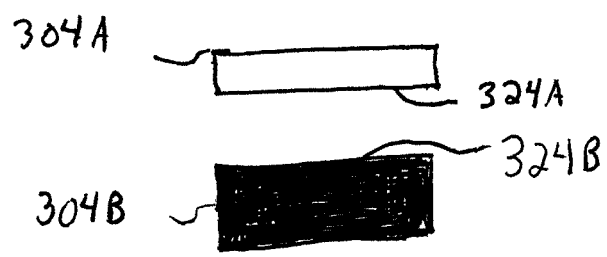
FIG. 3A is an end view of ribs of an exemplary guidewire torquer, in accordance with embodiments of the present invention.

FIG. 3A is an end view of an alternative embodiment of ribs 104 of FIG. 1, shown as ribs 304A, 304B. For ease of illustration, ribs 304 are shown in FIG. 3A as being substantially parallel to one another. It would be appreciated that this view of ribs 304 is merely for illustration purposes and does not limit the relationship of the two ribs to one another.

In the embodiments of FIG. 3A, ribs 304 are planar elements that extend from the inner surfaces 108 of the first and second halves 102. In contrast to the embodiments of FIGS. 2A-2B in which each rib has a concave area 220 that is proximate to the opposing half, in the embodiments of FIG. 3A each rib 304 has a generally rectangular shape. Each rib 304 has a substantially planar surface 324 that opposes the inner surface, and which is proximate to inner surface of the other torquer half.

Figure 3B:
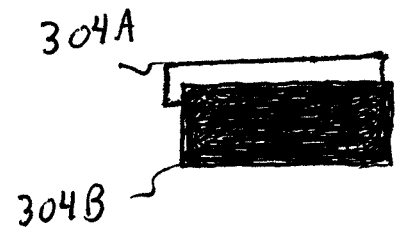
FIG. 3B is an end view of the ribs of FIG. 2A illustrating an exemplary rib overlap, in accordance with embodiments of the present invention.

As noted, FIG. 3A illustrates ribs 304 separated from one another. In contrast, FIG. 3B illustrates ribs 304 in a closed position. That is, FIG. 3B illustrates the position of ribs 304 relative to one another when halves 102 of wire torquer 100 are mated or closed together. Ribs 304 are offset from one another such that, in the end view of FIG. 3B, rib 304B is positioned in front of rib 304A. Additionally, when ribs 304 are in the closed position, the ribs are configured to engage and securely retain a section of the guidewire within torquer 100. More specifically, when wire torquer is closed, a section of a guidewire is clamped between the planar surfaces 324 of ribs 304 and the opposing inner surface.

As previously noted, the size (width, height, thickness, etc.) of wire retainers or ribs utilized in a wire torquer of the present invention may vary depending on a variety of factors, including the size of the guidewire to be used. In certain embodiments, the wire retainers are configured to accommodate guidewires having a diameter of approximately 0.01 inches to approximately 0.04 inches. It would be appreciated that these dimensions are merely illustrative.

In certain embodiments of the present invention, wire retainers 104 are unitary with a torquer half 102. That is, wire retainers 104 and a torquer half 102 may be manufactured as one unitary piece. In other embodiments, the wire retainers and a torquer half 102 may be separate pieces that are attached to one another during manufacture, or subsequent thereto.

As noted, wire retainers 104 within wire torquer 100 serve to retain a guidewire within the torquer. In certain embodiments of the present invention, to help secure the guidewire within torquer the surfaces of the wire retainers may be textured. Texturing the surfaces of wire retainers 104 that contact a guidewire enhances friction between the wire retainers and the guidewire.

FIG. 4 illustrates the shape of a portion of a guidewire 430 when positioned in a wire torquer, such as wire torquer 100, in accordance with embodiments of the present invention. For ease of illustration, wire torquer 100 has been omitted from FIG. 4.

As shown in FIG. 4, guidewire 430 has an undulating shape within wire torquer 100. Specifically, guidewire 430 has a series of high and low points 432 that correspond to areas in which wire retainers 104 engage the guidewire. The undulating shape of guidewire 430 substantially prevents longitudinal movement of the guidewire within torquer 100.

In embodiments of the present invention, the first and second halves of the wire torquer are secured together in the closed position by a locking mechanism. FIG. 5 illustrates a wire torquer 500 in accordance with embodiments of the present invention having an exemplary locking mechanism 550. As shown, wire torquer 500 comprises first and second torquer halves 502. Positioned on first half 502A is a protrusion 552, while positioned on second half 502B is an indentation 554. Protrusion 552 and indentation 554 collectively comprise locking mechanism 550.

As shown, protrusion 552 is positioned on inner surface 508A of first half 502A, and has a section 556 extending along elongate edge 560A of the first half. In the embodiment of FIG. 5, protrusion 552 also includes sections 558A, 558B that extend along lateral edges 562A, 564A of first half 502A.

Positioned on second half 502B is an indentation 554. As shown, indentation 554 is positioned on inner surface 508B of first half 502B, and has a section 566 extending along elongate edge 560B of the second half. In the embodiment of FIG. 5, indentation 554 also includes sections 568A, 568B that extend along lateral edges 562B, 564B of second half 502B. As such, indentation 554 and protrusion 552 are substantially reciprocal shapes, and positioned such that the indentation receives and secures protrusion therein. That is, protrusion 552 is held in indentation 554 through a compression or friction fit.

In certain embodiments, indentation 554 and protrusion 552 are sized such that inserting the protrusion into the protrusion secures in halves 502 together. For example, in one such embodiment, protrusion 552 may be larger than indentation 554, while in another or additional embodiment protrusion 552 and/or indentation 554 are formed from an elastic material that, when the elements are forced together, further enhances engagement between the two elements.

It would be appreciated that locking mechanism 550 of FIG. 5 is merely illustrative of one of a number of locking mechanisms that may be implemented in embodiments of the present invention. For example, in alternative embodiments of the present invention, the locking mechanism may comprise other types of snap-lock connectors. In another embodiment, the locking mechanism may be a magnetic lock in which a magnet is disposed in or on first inner surface 508A. In such embodiments, a magnetic material, such as a piece of metal, is at least one of integrated in, or attached to, surface 508B of second half 502B so as to attract the magnet in first half 502A. Additionally, FIG. 5 illustrates a specific embodiment having one protrusion 552 and a corresponding indentation 554. It would be appreciated that embodiments of the present invention may also use multiple separated protrusions/indentations for the locking mechanism.

Figure 6A:
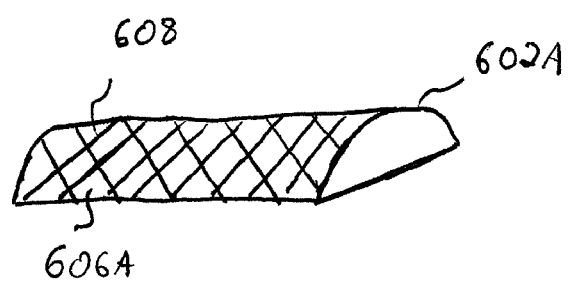
FIG. 6A is a perspective view of a half of a guidewire torquer having a textured surface, in accordance with embodiments of the present invention.
Figure 6B:
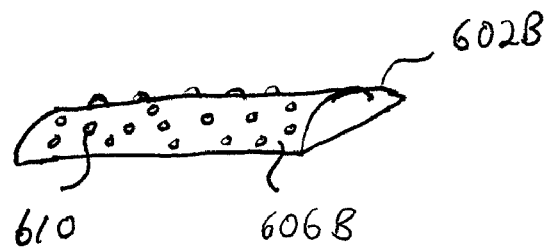
FIG. 6B is a perspective view of a half of a guidewire torquer having a textured surface, in accordance with embodiments of the present invention.

During use of a wire torquer in accordance with embodiments of the present invention, a surgeon must grip and apply force to the torquer so as to manipulate the attached guidewire. In certain embodiments of the present invention, the outer surface of the torquer is textured to increase friction between the device and the surgeon's hand, tool, etc. FIGS. 6A and 6B illustrate two exemplary textures for the outer surface of a torquer. More specifically, FIG. 6A illustrates a guidewire torquer half 602A in which the outer surface 606A includes a pattern of grooves 608 formed therein. Grooves 608 may be formed in a number of different patterns, including an angled pattern or an X pattern. FIG. 6B illustrates an alternative guidewire torquer half 602B in which the outer surface 606B is textured for increased friction through the use of a number of raised sections or bumps 610.

In accordance with certain embodiments of the present invention, the first and second halves of the guidewire torquer are separately identifiable to allow for visual correlation of manipulation of the device to torque applied to the wire. In one embodiment, this visual correlation is provided by making the first and second halves different colors. In other embodiments, the first and second halves may have identification markings. In still further embodiments, one or both of the halves may include a scale or other mechanism that allows the surgeon to visualize or quantify the torque that is applied to the guidewire.

Embodiments of the present invention have been described above with reference to the structure of the guidewire torquer. It would be appreciated that embodiments of the present invention also encompass methods of use of the guidewire torquer. For example, in certain embodiments the method for using the guidewire torquer comprises deploying the torquer from the side of a medical guidewire, manipulating the torquer to position a distal end of the guidewire in a patient; and detaching the torquer from the medical guidewire. In further embodiment in which the torquer comprises an elongate body comprising first and second elongate halves having an outer surface and inner surfaces, wherein the first and second halves are coupled to one another such that the inner surfaces to mate with one another, and wherein the mated surfaces are substantially parallel to the longitudinally axis of the body, deploying the torquer from the wide of the medical guidewire comprises positioning the mating surfaces of the torquer on substantially opposing sides of the guidewire; mating the inner surfaces of the torquer to one another; and securing the first and second halves in the mated configuration.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A side-deployable medical guidewire torquer, comprising:
    an elongate body comprising first and second halves having an outer surface and inner surfaces, wherein the first and second halves are coupled to one another such that the inner surfaces to mate with one another, and wherein the mated surfaces are substantially parallel to the longitudinally axis of the body;
    a plurality of wire retainers disposed on the inner surfaces of both of the first and second halves configured to engage a guidewire positioned between the halves; and
    a releasable lock mechanism configured to secure mechanically the first and second halves in the mated configuration;
    wherein the guidewire is retained entirely between the wire retainers and does not contact the inner surfaces of the first and second halves.

2. The wire torquer of claim 1, wherein the elongate body is substantially cylindrical along its longitudinal axis, and wherein the inner surfaces are substantially planar.

3. The guidewire torquer of claim 1, wherein the wire retainers are ribs extending from the inner surface having a concave area that is proximate to the opposing half, and wherein the concave area engages the guidewire.

4. The guidewire torquer of claim 1, wherein the wire retainers are ribs extending from the inner surface having a generally planar surface that is proximate to the opposing half, and wherein the planar surface engages the guidewire.

5. The guidewire torquer of claim 1, wherein the wire retainers extending from the inner surface of the first half are offset from the wire retainers extending from the inner surface of the second half.

6. The guidewire torquer of claim 5, wherein the wire retainers have a textured surface to increase friction between the retainers and the guidewire.

7. The guidewire torquer of claim 1 wherein the lock mechanism comprises:
   a protrusion extending from the inner surface of the first half; and
   an indentation in the inner surface of the second half configured to receive and securely retain the protrusion therein through compression or friction fit when the first and second halves are manually pressed together.

8. The guidewire torquer of claim 7, comprising:
   a plurality of protrusions extending from the from the inner surface of the first half; and
   a plurality of indentations in the inner surface of the second half each configured to receive and securely retain a protrusion of the first half therein.

9. The guidewire torquer of claim 1, wherein the lock mechanism comprises a magnetic lock comprising:
   one or more magnets at least one of integrated in or attached to the surface of the first body; and
   a magnetic material at least one of integrated in or attached to the surface of the second body half to attract the magnet in the first body half.

10. The guidewire torquer of claim 1, further comprises:
    a first arm disposed on the outer surface of the first body half; and
    a second arm disposed on the outer surface of the second body half, wherein the arms allow a surgeon to mate the first and second halves of the torque.

11. The guidewire torquer of claim 1, wherein the outer surfaces of the first and second halves are textured.

12. The guidewire torquer of claim 11, wherein the texture of the outer surfaces comprises a plurality of grooves.

13. The guidewire torquer of claim 11, wherein the texture of the outer surfaces comprises a plurality of raised protrusions.

14. The guidewire torquer of claim 1, wherein the first and second halves are separately identifiable so as to allow for visual correlation of torque applied to the wire.

15. A method for using a guidewire torquer, comprising:
    deploying the torquer from the side of a medical guidewire, the torquer comprising an elongate body including first and second elongate halves having an outer surface and inner surfaces, a plurality of wire retainers disposed on the inner surfaces of both of the first and second halves configured to engage a guidewire positioned between the halves, wherein the guidewire is retained entirely between the wire retainers and does not contact the inner surfaces of the first and second halves;
    manipulating the torquer to position a distal end of the guidewire in a patient; and
    detaching the torquer from the medical guidewire.

16. The method of claim 15, wherein the first and second halves are coupled to one another such that the inner surfaces to mate with one another, and wherein the mated surfaces are substantially parallel to the longitudinally axis of the body, and wherein deploying the torquer from the wide of the medical guidewire comprises:
    positioning the mating surfaces of the torquer on substantially opposing sides of the guidewire;
    mating the inner surfaces of the torquer to one another; and
    securing the first and second halves in the mated configuration.

17. The guidewire torquer of claim 3, wherein the concave areas create a space in which the guidewire is positioned when the ribs are in a closed position.

* * * * *